US012587844B2

(12) United States Patent
Marterstock et al.

(10) Patent No.: US 12,587,844 B2
(45) Date of Patent: Mar. 24, 2026

(54) DEVICE AND METHOD FOR THE AUTHENTICATION OF A USER OF A MEDICAL DEVICE

(71) Applicant: FRESENIUS MEDICAL CARE DEUTSCHLAND GMBH, Bad Homburg (DE)

(72) Inventors: Stefan Konrad Marterstock, Bad Homburg (DE); Kevin Heiko Hartmann, Bad Homburg (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 634 days.

(21) Appl. No.: 18/010,470

(22) PCT Filed: Jun. 21, 2021

(86) PCT No.: PCT/EP2021/066776
§ 371 (c)(1),
(2) Date: Dec. 15, 2022

(87) PCT Pub. No.: WO2021/259837
PCT Pub. Date: Dec. 20, 2021

(65) Prior Publication Data
US 2023/0164552 A1    May 25, 2023

(30) Foreign Application Priority Data
Jun. 22, 2020    (DE) ..................... 10 2020 207 697.9

(51) Int. Cl.
*H04W 12/06*        (2021.01)
*A61M 1/14*         (2006.01)
(Continued)

(52) U.S. Cl.
CPC .............. *H04W 12/06* (2013.01); *A61M 1/14* (2013.01); *G16H 40/67* (2018.01); *H04B 11/00* (2013.01);
(Continued)

(58) Field of Classification Search
CPC ........ H04W 12/06; G16H 40/67; A61M 1/14; H04B 11/00
See application file for complete search history.

(56) References Cited

U.S. PATENT DOCUMENTS

| | | | |
|---|---|---|---|
| 5,309,144 A | 5/1994 | Lacombe et al. | |
| 2014/0068751 A1 | 3/2014 | Last | |

(Continued)

OTHER PUBLICATIONS

International Preliminary Report on Patentability issued in corresponding International Patent Application No. PCT/EP2021/066776 (with English translation) mailed Jan. 5, 2023 (19 pages).

(Continued)

*Primary Examiner* — Curtis B Odom
(74) *Attorney, Agent, or Firm* — Kilyk & Bowersox, P.L.L.C.

(57) ABSTRACT

A treatment system (100) for treating a patient comprises a medical device (10) and a portable authentication device (20), wherein the medical device (10) is adapted to output an acoustic signal when a wireless communication connection between the medical device (10) and the portable authentication device (20) is successfully established, the portable authentication device (20) is adapted to receive the acoustic signal, to generate, based on the received acoustic signal, a signal containing a signal corresponding to the received acoustic signal, and to wirelessly transmit the generated signal to the medical device (10), and the medical device (10) is adapted to determine whether or not the portable authentication device (20) is located at a position where acoustic communication between the medical device (10)
(Continued)

and the portable authentication device (20) is possible, depending on whether or not it receives the signal containing the signal corresponding to the acoustic signal received by the portable authentication device (20).

17 Claims, 1 Drawing Sheet

(51) Int. Cl.
      *G16H 40/67*          (2018.01)
      *H04B 11/00*          (2006.01)
(52) U.S. Cl.
      CPC ............... *A61M 2205/3561* (2013.01); *A61M 2205/3576* (2013.01); *A61M 2205/502* (2013.01); *A61M 2205/52* (2013.01); *A61M 2205/6009* (2013.01); *A61M 2205/6018* (2013.01)

(56)                      References Cited

U.S. PATENT DOCUMENTS

| | | |
|---|---|---|
| 2014/0148104 A1 | 5/2014 | Marterstock |
| 2014/0258392 A1 | 9/2014 | Barth et al. |
| 2016/0234208 A1 | 8/2016 | Daley et al. |
| 2017/0295466 A1 | 10/2017 | Strutt et al. |
| 2018/0225432 A1 * | 8/2018 | Suarez .................. G06F 21/305 |
| 2020/0114054 A1 | 4/2020 | Medina et al. |

OTHER PUBLICATIONS

International Search Report and Written Opinion issued in corresponding International Patent Application No. PCT/EP2021/066776 (with English translation of International Search Report) mailed Sep. 22, 2021 (29 pages).

* cited by examiner

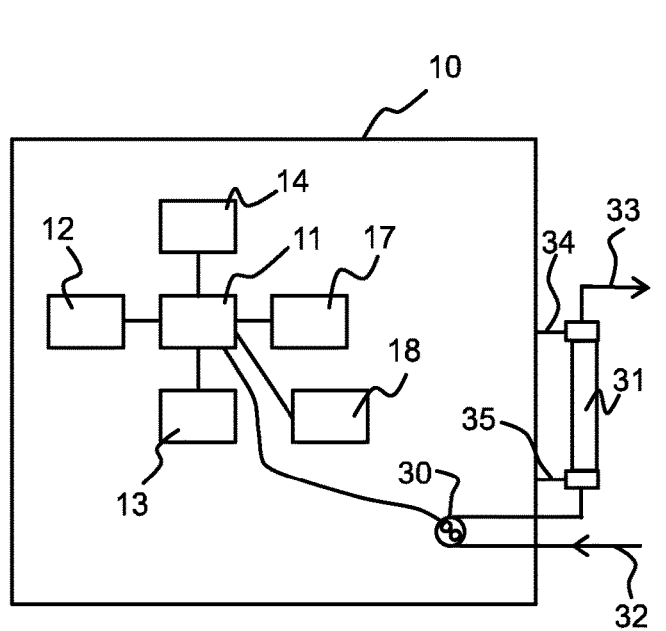
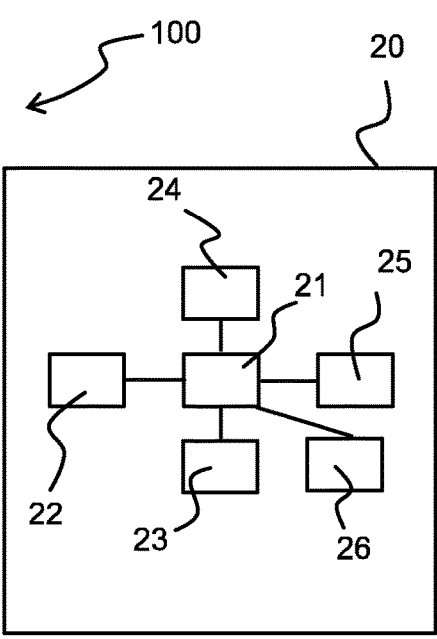

DEVICE AND METHOD FOR THE AUTHENTICATION OF A USER OF A MEDICAL DEVICE

This application is a National Stage Application of PCT/ EP2021/066776, filed Jun. 21, 2021, which claims priority to German Patent Application No. 10 2020 207 697.9, filed Jun. 22, 2020.

BACKGROUND OF THE INVENTION

The present invention relates to a device and a method for the authentication of a user of a medical device. The present invention relates in particular to a medical device for a treatment system, a treatment system for treating a patient comprising a medical device and a portable authentication device, and a method for verifying the authentication of a portable authentication device for a treatment system. Here, the medical device and the treatment system are preferably used to carry out a dialysis treatment of a patient.

In this context, medical devices are understood to mean, in particular, devices for conducting, treating and/or distributing liquids and/or gases, in which a fluid is transported between a patient and a fluid treatment component and/or a fluid source via a fluid line.

Medical devices are also to be understood as meaning, in particular, fluid treatment devices, such as, for example, blood treatment devices, in which a fluid from a patient is supplied via a fluid line to a fluid treatment component, treated by the fluid treatment component and returned to the patient via the fluid line, which can be divided into an arterial and a venous branch. Examples of such blood treatment devices are in particular haemodialysis devices.

Dialysis is a procedure for purifying the blood of patients with acute or chronic renal failure. In principle, a distinction is made here between procedures with an extracorporeal blood circulation, such as hemodialysis, hemofiltration or hemodiafiltration, and peritoneal dialysis, which does not have an extracorporeal blood circulation.

The procedures of haemodialysis, haemofiltration and haemodiafiltration, hereinafter referred to as haemodialysis, are generally carried out using automated haemodialysis devices such as are marketed, for example, by the applicant under the name 5008.

The peritoneal dialysis procedure is generally performed with the aid of automated peritoneal dialysis devices such as are marketed, for example, by the applicant under the name sleep.safe.

Dialysis devices, as an example of complex medical devices, have a wide range of functions for performing dialysis treatment. In order to control these functions, medical devices such as dialysis devices are equipped with at least one control device, which can be designed as a central processing unit or a microcontroller, and which controls the medical device using software programs stored in a memory device of the medical device. For the operation of such devices, they have an input/output device, which can be designed as a touch screen, for example, or input and output devices provided separately from one another. By means of the input/output device, for example, patient data, such as name, age, patient identification number, patient history, and the like, can also be entered by a user and stored in the memory device. Operating parameters of the medical device recorded during a treatment of the patient can also be stored automatically and assigned to the patient in the memory device. The data stored in the memory device, in particular the patient data and the operating parameters, can then be retrieved at a later time by the same user or by another user by means of the input/output device.

The treatment of patients by means of dialysis devices represents a serious intervention in the patient's blood circulation. It is therefore necessary that the corresponding dialysis devices can only be set up and adjusted by specially trained operating personnel. Since a common dialysis station may have different types of dialysis devices, it is possible that certain dialysis nurses are not trained on all dialysis devices and therefore an operation, especially the adjustment of critical operating parameters, should only be carried out by appropriately trained personnel.

Furthermore, it should be avoided that the patients themselves or visitors or third parties, can manipulate the dialysis devices during a dialysis procedure, either intentionally or unintentionally. In addition, unauthorized persons should be prevented from gaining access to the patient data stored in the memory device and/or the operating parameters assigned to the patient.

To prevent a complex medical device for the treatment of a patient, such as a dialysis device, from being operated by an unauthorized person, such as a patient or insufficiently trained personnel, measures are usually taken to ensure that only authorized persons can set or change operating parameters of the medical device and have access to the data stored in the memory device. This may, for example, require a user to have to log on or authenticate to the medical device by entering a user ID and a password assigned to the user ID before he gains access the data stored in the memory device or can set or change the operating parameters of the medical device.

To enhance the convenience of operating medical devices, portable authentication devices are also used which are adapted to communicate wirelessly with the medical device and to transmit an authentication signal containing information identifying the user of the portable authentication device or the portable authentication device to the medical device. In this case however, there is the risk that an unauthorized user may gain unauthorized access to the medical device, for example by performing a man-in-the-middle attack, and thus be able to set and change the operating parameters of the medical device or access the data stored in the memory device. In the man-in-the-middle attack, the attacker, by means of a corresponding device, logically switches into the communication channel between the portable authentication device and the medical device and can thus read out the data traffic, including the authentication signal, between the portable authentication device and the medical device. In this way, the attacker can authenticate to the medical device at a later time using the read-out authentication signal and thus control the medical device and/or set or change the operating parameters of the medical device.

SUMMARY OF THE INVENTION

The object of the present invention is therefore to further improve the operating safety of medical devices and the protection against unauthorized access to the medical devices and thus to further increase patient safety.

The solution to this problem is provided by a treatment system for treating a patient as described herein, a medical device as described herein and a method for verifying the authentication of a portable authentication device for a treatment system as described herein. Preferred embodiments of the invention are the subject of the subclaims and the present description of the invention.

A treatment system for treating a patient according to an embodiment comprises a medical device and a portable authentication device, wherein the medical device and the portable authentication device are adapted to communicate wirelessly with each other, the medical device is adapted to output an acoustic signal when a wireless communication connection between the medical device and the portable authentication device is successfully established, the portable authentication device is adapted to receive the acoustic signal, to generate, based on the received acoustic signal, a signal containing a signal corresponding to the received acoustic signal, and to wirelessly transmit the generated signal to the medical device, and the medical device is adapted to determine whether or not the portable authentication device is located at a position where acoustic communication between the medical device and the portable authentication device is possible, depending on whether or not it receives the signal containing the signal corresponding to the acoustic signal received by the portable authentication device.

A treatment system for treating a patient according to a different embodiment comprises a medical device and a portable authentication device, wherein the medical device and the portable authentication device are adapted to communicate wirelessly with each other, the medical device is adapted to wirelessly transmit a signal containing a signal corresponding to an acoustic signal when a wireless communication connection between the medical device and the portable authentication device is successfully established, the portable authentication device is adapted to receive the signal containing the signal corresponding to the acoustic signal, to generate, based on the received signal, an acoustic signal corresponding to the signal corresponding to the acoustic signal, and to output the generated acoustic signal to the medical device, and the medical device is adapted to determine whether or not the portable authentication device is located at a position where acoustic communication between the medical device and the portable authentication device is possible, depending on whether or not it receives the acoustic signal.

A treatment system for treating a patient according to a further embodiment comprises a medical device and a portable authentication device, wherein the medical device and the portable authentication device are adapted to communicate wirelessly with each other, the portable authentication device is adapted to wirelessly transmit a signal containing a signal corresponding to an acoustic signal when a wireless communication connection between the medical device and the portable authentication device is successfully established, the medical device is adapted to receive the signal containing the signal corresponding to the acoustic signal, to generate, based on the received signal, an acoustic signal corresponding to the signal corresponding to the acoustic signal, and to output the generated acoustic signal to the portable authentication device, the portable authentication device is adapted to receive the acoustic signal, and to wirelessly transmit a signal to the medical device indicating that the portable authentication device has received the acoustic signal upon receipt of the acoustic signal, and the medical device is adapted to determine whether or not the portable authentication device is located at a position where acoustic communication between the medical device and the portable authentication device is possible, depending on whether or not it receives the signal indicating that the portable authentication device has received the acoustic signal.

A treatment system for treating a patient according to another, different embodiment comprises a medical device and a portable authentication device, wherein the medical device and the portable authentication device are adapted to communicate wirelessly with each other, the portable authentication device is adapted to output a predetermined acoustic signal, preferably a predetermined sequence of tones, when a wireless communication connection between the medical device and the portable authentication device is successfully established, and the medical device is adapted to determine whether or not the portable authentication device is located at a position where acoustic communication between the medical device and the portable authentication device is possible, depending on whether or not it receives the predetermined acoustic signal.

According to the treatment systems for treating a patient according to the invention, the functional safety of the medical device can be ensured and a man-in-the-middle attack can be made more difficult when authenticating the portable authentication device by the additional use of an acoustic communication channel to the usual communication channel via wireless signals. In addition, the user is additionally informed about an authentication process taking place by outputting the acoustic signal by means of the medical device or the portable authentication device, so that, if he does not authenticate himself, he can, if applicable, take measures against a man-in-the-middle attack.

According to an embodiment, the acoustic signal is a random or predetermined sequence of tones, which may have several different tones, which are output sequentially, and the signal containing the signal corresponding to the acoustic signal may contain a signal corresponding to the random or the predetermined sequence of tones.

In the case that the acoustic signal is the predetermined sequence of tones, the sequence of tones may be determined by an individual identification number that uniquely identifies the medical device. In this way, the user can advantageously quickly recognize which medical device he is authenticating to.

According to an embodiment, the medical device and the portable authentication device are adapted to communicate wirelessly with each other via a common radio standard and/or the medical device and the portable authentication device are adapted to communicate wirelessly with each other via an infrared signal.

In a preferred embodiment, the medical device is adapted to transmit wirelessly an information-retrieval signal for retrieving authentication information to the portable authentication device and to receive an authentication signal wirelessly, wherein the portable authentication device is adapted to transmit, cyclically and/or after receipt of the information-retrieval signal, an authentication signal containing information identifying the portable authentication device, the medical device is adapted to, upon receipt of the authentication signal from the portable authentication device, perform an authentication in which it is verified whether or not the authentication signal is assigned to a user registered in an authorization database or to a portable authentication device registered in the authorization database, and whether or not the portable authentication device is located at a position where an acoustic communication between the medical device and the portable authentication device is possible, and to determine that the authentication is successful if the authentication signal is assigned to a user registered in an authorization database or to a portable authentication device registered in the authorization database and the portable authentication device is located at a position where an acoustic communication between the medical device and the portable authentication device is possible.

With this preferred embodiment, authentication is thus performed using a two-channel authentication process, which uses a first communication channel for the transmission of wireless signals, in particular data signals, such as the information-retrieval signal for retrieving authentication information and the authentication signal, and a second communication channel for the transmission of the acoustic signal. In this way, a man-in-the-middle attack, which is only performed on one of the two communication channels, can be prevented and thus patient safety can be increased.

The authorization database may be stored in a memory device of the medical device or in a memory device in communication with a control device of the medical device, an individual code word being stored in the authorization database for each of a plurality of different portable authentication devices together with one or more authorizations assigned to the respective individual code word. In the case of a preferred embodiment, an individual code word can also be stored in the authorization database for each individual user together with one or more authorizations which are assigned to the respective individual code word. In this case, the authentication signal sent by the portable authentication device contains the respective individual code word. In this way, the user operating the medical device can be identified by a predetermined assignment of the portable authentication device to a particular user at fixed times or by assigning the code word to the user. The authorizations may include an authorization that entitles the respective user, such as a physician or a fully trained and correspondingly certified dialysis nurse, to access all functions of the medical device, and respective authorizations that entitle the respective user only to access certain functions of the medical device which are matched to the level of training of the user.

In particular, if the medical device determines that the authentication is successful, the medical device determines that the user, to whom the corresponding authentication signal is assigned, is authorized to operate the specific medical device, and enables access to the medical device within the scope of the authorizations assigned to the authentication signal in the authorization database.

According to a preferred embodiment, the medical device further comprises a memory device, in which patient data and/or operating parameters of the medical device assigned to the patient data, which parameters were recorded during a treatment of the patient, can be stored or are stored, and an input/output device comprising a display for displaying the patient data and/or the operating parameters of the medical device assigned to the patient data, wherein a user can only cause the patient data stored in the memory device and/or the operating parameters of the medical device assigned to the patient data and stored in the memory device to be displayed on the display of the input/output device by means of an input using the input/output device if the medical device determines that the authentication is successful.

Thus, according to this preferred embodiment, unauthorized access to the patient data stored in the memory device of the medical device, such as name, age, patient identification number, patient history, and the like, as well as unauthorized access to operating parameters of the medical device recorded during a treatment of the patient and stored in the memory device of the medical device and assigned to the patient, can be prevented or at least made more difficult.

In a particularly preferred embodiment, the patient data and/or the operating parameters assigned to the patient data and stored in the memory device of the medical device can be transferred by a user to a memory unit of the portable authentication device by means of the wireless communication connection between the medical device and the portable authentication device only if the medical device determines that the authentication is successful.

According to another preferred embodiment, the medical device comprises a memory device in which an individual identification number is stored which uniquely identifies the medical device, wherein the medical device is adapted to also transmit, in the signal containing a signal corresponding to the acoustic signal, a signal corresponding to the individual identification number stored in the memory device, and the portable authentication device comprises an input/output device having a display and is adapted to output the individual identification number on the display after receipt of the signal transmitted by the medical device. By outputting the individual identification number on the display of the portable authentication device, the user can identify the medical device and, if applicable, prevent access to the medical device by an unauthorized user.

In this other preferred embodiment, the medical device is adapted to transmit wirelessly an information-retrieval signal for retrieving authentication information to the portable authentication device and to receive wirelessly an authentication signal, the portable authentication device is adapted to transmit cyclically and/or after receiving the information-retrieval signal an authentication signal containing information identifying the portable authentication device. In this case, the medical device is adapted to perform an authentication upon receipt of the authentication signal from the portable authentication device, in which it is verified whether or not the authentication signal is assigned to a user registered in an authorization database or to a portable authentication device registered in the authorization database, and whether or not the portable authentication device is located at a position at which acoustic communication between the medical device and the portable authentication device is possible, and to determine that the authentication is successful if the authentication signal is assigned to a user registered in an authorization database or to a portable authentication device registered in the authorization database and the portable authentication device is located at a position where acoustic communication between the medical device and the portable authentication device is possible, wherein in the memory device patient data and/or operating parameters of the medical device assigned to the patient data, which have been recorded during a treatment of the patient, can be stored or are stored, and the medical device further comprises an input/output device having a display for displaying the patient data and/or the operating parameters of the medical device assigned to the patient data, wherein a user can only cause the patient data stored in the memory device and/or the operating parameters of the medical device assigned to the patient data and stored in the memory device to be displayed on the display of the input/output device by means of an input using the input/output device if the medical device determines that the authentication is successful.

Preferably, the patient data and/or the operating parameters assigned to the patient data, which are stored in the memory device of the medical device can be transferred by a user into the memory unit of the portable authentication device by means of the wireless communication connection between the medical device and the portable authentication device only if the medical device determines that the authentication is successful.

In a particularly preferred embodiment, the portable authentication device is designed as a mobile telephone, in particular as a smartphone, or as a portable computer. The embodiment of the portable authentication device as a smartphone is advantageous in two ways. On the one hand, a smartphone already contains a microphone and a loudspeaker, and on the other hand, smartphones are usually carried by their users at all times, so that there is no need to carry another device for authentication at the medical device.

According to an embodiment, the medical device is a dialysis device that is adapted to perform dialysis treatment.

A medical device according to an embodiment for a treatment system is adapted to communicate wirelessly with a portable authentication device and, when a wireless communication connection is successfully established between the medical device and the portable authentication device, to output an acoustic signal and to determine whether or not the portable authentication device is located at a position where acoustic communication between the medical device and the portable authentication device is possible, depending on whether or not the medical device receives a signal wirelessly transmitted by the portable authentication device and containing a signal corresponding to the transmitted acoustic signal.

A medical device according to a different embodiment for a treatment system is adapted to communicate wirelessly with a portable authentication device and, when a wireless communication connection between the medical device and the portable authentication device is successfully established, to wirelessly transmit a signal containing a signal corresponding to an acoustic signal, and to determine whether or not the portable authentication device is located at a position where acoustic communication between the medical device and the portable authentication device is possible, depending on whether or not the medical device receives an acoustic signal output by the portable authentication device corresponding to the signal corresponding to the acoustic signal.

A medical device according to a further embodiment for a treatment system is adapted to communicate wirelessly with a portable authentication device and, when a wireless communication connection between the medical device and the portable authentication device is successfully established, to receive a signal wirelessly transmitted by the portable authentication device and containing a signal corresponding to an acoustic signal, to generate, based on the received signal, an acoustic signal corresponding to the signal corresponding to the acoustic signal, and to output the generated acoustic signal to the portable authentication device, and to determine whether or not the portable authentication device is located at a position where acoustic communication between the medical device and the portable authentication device is possible, depending on whether or not the medical device receives a signal wirelessly transmitted by the portable authentication device indicating that the portable authentication device has received the acoustic signal.

A medical device according to another different embodiment for a treatment system is adapted to communicate wirelessly with a portable authentication device and, when a wireless communication connection between the medical device and the portable authentication device is successfully established, to receive a predetermined acoustic signal output by the portable authentication device, preferably a predetermined sequence of tones, and, depending on whether or not the medical device receives the predetermined acoustic signal, to determine whether or not the portable authentication device is at a position where acoustic communication between the medical device and the portable authentication device is possible.

A method according to an embodiment for verifying the authentication of a portable authentication device for a treatment system described above comprises outputting an acoustic signal by the medical device, receiving the acoustic signal by the portable authentication device, generating, based on the received acoustic signal, by the portable authentication device, a signal containing a signal corresponding to the received acoustic signal, and wirelessly transmitting the generated signal to the medical device by the portable authentication device, and determining, by the medical device, depending on whether or not it receives the signal containing the signal corresponding to the acoustic signal received by the portable authentication device, whether or not the portable authentication device is located at a position where acoustic communication between the medical device and the portable authentication device is possible.

A method according to another embodiment for verifying the authentication of a portable authentication device for a treatment system described above comprises wirelessly transmitting, by the medical device, a signal containing a signal corresponding to an acoustic signal, receiving, by the portable authentication device, the signal corresponding to the acoustic signal, generating, based on the received signal, by the portable authentication device, an acoustic signal corresponding to the signal corresponding to the acoustic signal and outputting the generated acoustic signal to the medical device, and determining, by the medical device, depending on whether or not it receives the acoustic signal, whether or not the portable authentication device is located at a position where acoustic communication between the medical device and the portable authentication device is possible.

A method according to a further embodiment for verifying the authentication of a portable authentication device for a treatment system comprises wirelessly transmitting, by the portable authentication device, a signal containing a signal corresponding to an acoustic signal, receiving, by the medical device, the signal containing the signal corresponding to the acoustic signal, generating, by the medical device, based on the received signal, an acoustic signal corresponding to the signal corresponding to the acoustic signal, and outputting, by the medical device, the generated acoustic signal to the portable authentication device, wirelessly transmitting, by the portable authentication device, a signal indicating that the portable authentication device has received the acoustic signal, to the medical device if the portable authentication device has received the acoustic signal from the medical device, and determining, by the medical device, depending on whether or not it receives the signal indicating that the portable authentication device has received the acoustic signal, whether or not the portable authentication device is located at a position where acoustic communication between the medical device and the portable authentication device is possible.

A method according to a further different embodiment for verifying the authentication of a portable authentication device for a treatment system comprises outputting a predetermined acoustic signal, preferably a predetermined sequence of tones, by the portable authentication device, and determining, by the medical device, depending on whether or not it receives the predetermined acoustic signal, whether or not the portable authentication device is located at a position where acoustic communication between the medical device and the portable authentication device is possible.

Further possible preferred embodiments of the method according to the invention can be derived from the description of the system according to the invention and its preferred embodiments.

Further preferred embodiments of the system and method according to the invention result from the following description of the embodiments in connection with the FIGURE and its description. Identical components of the embodiments are essentially identified by identical reference number, unless otherwise described or unless this is otherwise apparent from the context. It shows:

BREIF DESCRIPTION OF THE DRAWINGS

FIG. 1 schematically a treatment system according to an embodiment with a medical device and an authentication device.

DETAILED DESCRIPTION OF THE INVENTION

FIG. 1 illustrates a treatment system for a patient according to an embodiment which is usually used in a clinical facility, for example, in a dialysis station, in which a plurality of medical devices is provided for treating patients. The treatment system 100 comprises a medical device 10 for treating a patient out of the plurality of medical devices for treating a patient and a portable authentication device 20 carried by an operator or a user of the medical device 10, such as a physician or clinical staff member authorized to operate the medical device 10.

The medical device 10 is designed as a haemodialysis device or as a dialysis device with a control device 11, as well as a communication device 12, a memory device 13 and an input/output device 14 having a display, for example in the form of a touch screen, which are connected to the control device 11. In other, not shown embodiments, the medical device may also be designed as a peritoneal dialysis device or as a device for treating patients with acute kidney damage by continuous renal replacement therapy, which also have a control device, as well as a communication device, a memory device and an input/output device having a display, which are connected to the control device.

The control device 11, which can be designed, for example, as a central processing unit or as a microcontroller, is adapted to control the components of the medical device 10, for example, by means of software programs running on the control device 11, which are stored in the memory device 13, and to call up or control various functions of the medical device 10 and set operating parameters of the medical device 10 depending on an input by an authenticated user by means of the input/output device 14.

For dialysis treatment, the medical device 20 designed as a haemodialysis device has in particular a blood pump 30 connected to the control device 11 and a dialysis filter 31, which, in the case of treatment of a not depicted patient, are components of an extracorporeal blood circuit which also has an arterial blood line 32 for draining off the patient's blood and a venous line 33 for returning the blood to the patient. In operation, the blood from the patient is fed via the arterial blood line 32 to the blood pump 30 and pumped by the blood pump 30 through the dialysis filter 31, which has a semi-permeable membrane that semi-permeably separates the extracorporeal blood circuit from a dialysate circuit. Dialysate is pumped through the dialysis filter 31 via dialysate lines 34, 35 connected to the dialysis filter 31, where a diffusive mass transfer with the patient's blood takes place via the semipermeable membrane of the dialysis filter 31. By establishing a pressure gradient from the blood side of the dialysis filter to the dialysate side of the dialysis filter 31 in such a way that a negative pressure prevails on the dialysate side, plasma water is pressed out of the blood into the dialysate, thus draining the patient's blood.

In order to enable an authentication of a user to be carried out, an authorization database is stored in the memory device 13 of the medical device 10 or in a non-displayed external memory device in communication with the control device 11, in which an individual code word is stored for each of the portable authentication devices 20 used in the clinical facility together with one or more authorizations assigned to the respective individual code word. In a preferred embodiment, an individual code word for each individual user together with one or more authorizations assigned to the respective individual code word may be stored in the authorization database. In this way, the user operating the medical device 10 can be identified by a pre-defined assignment of the portable authentication device 20 to a specific user at specified times or by assigning the code word to the user. The authorizations may include an authorization entitling the respective user, such as a physician or a fully trained and correspondingly certified dialysis nurse, to access all functions of the medical device, and respective authorizations entitling the respective user only to access certain functions of the medical device which are matched o the level of training of the user.

The portable authentication device 20 comprises a control unit 21, a communication unit 22, a memory unit 23, an input/output unit 24 such as a touch screen, a speaker 25 and a microphone 26. In this regard, the portable authentication device 20 can be designed, for example, as a portable computer, for example, as a tablet, or in a preferred embodiment, as a mobile radio device, in particular as a smartphone. The design of the portable authentication device 20 as a smartphone is advantageous in two respects. On the one hand, a microphone and a loudspeaker are already installed in a smartphone, and on the other hand, smartphones are usually always carried along by their users, so that the carrying along of a further device for authentication at the medical device 10 can be omitted.

The medical device 10 is adapted to communicate wirelessly with the portable authentication device 20 by means of the communication device 12 under control of the control device 11 by sending signals, in particular data signals, and receiving signals, in particular data signals. The portable authentication device 20 is adapted to communicate wirelessly with the medical device 10 by means of the communication unit 22 by transmitting signals, in particular data signals, and receiving signals, in particular data signals. Accordingly, the communication unit 22 and the portable authentication device 20 are adapted to communicate with the same signal types as the communication device 12 and the medical device 10, for example in the same frequency band using the same communication protocol. The wireless communication between the communication device 12 of the medical device 10 and the communication unit 22 of the portable authentication device 20 can be performed using known communication standards. For example, wireless communication can be performed using radio protocols such as the zigbee standard, WLAN, Bluetooth, and other known radio protocols.

The medical device 10 also comprises a loudspeaker 17 and a microphone 18, which are also connected to the control device 11. In the event that a malfunction of a component of the medical device 10 is detected by the control device 11 of the medical device 10 during operation, the loudspeaker 17 can be used, for example, to output an alarm tone to inform the user of the malfunction. The microphone 18 can serve, for example, as an additional input device with which commands to the control device 11 or the medical device 10 can be input in the form of speech.

Preferably, the authentication of a user is performed using a two-channel authentication process comprising a first communication channel for transmitting wireless signals, in particular data signals, and a second communication channel for transmitting an acoustic signal.

For authentication using the first communication channel, the medical device 10 in accordance with an embodiment transmits an information-retrieval signal, in particular a data signal for retrieval of authentication information, wirelessly to the portable authentication device 20 by means of the communication device 12 under control of the control device 11, after a wireless communication connection between the medical device 10 and the portable authentication device 20 has been successfully established. On receipt of the information-retrieval signal, the portable authentication device 20 transmits to the medical device 10 by means of the communication unit 22, under control of the control unit 21, an authentication signal which contains the code word or information which identifies the portable authentication device 20 and which is stored in the memory unit 23. When the authentication signal is received, the medical device 10 verifies, by means of the authorization database, whether or not the portable authentication device 20 is a portable authentication device 20 registered in the authorization database, and can thus determine whether or not the user to whom the corresponding authentication signal is assigned is in principle authorized to operate the specific medical device 10.

According to another embodiment, in the authentication using the first communication channel, after a wireless communication connection between the medical device 10 and the portable authentication device 20 is successfully established, the portable authentication device 20 periodically transmits the authentication signal containing the code word or information identifying the portable authentication device 20 stored in the memory unit 23 to the medical device 10. When the authentication signal is received, the medical device 10 verifies, on the basis of the authorization database, whether or not the portable authentication device 20 is a portable authentication device 20 registered in the authorization database, and can thus determine whether or not the user to whom the corresponding authentication signal is assigned is in principle authorized to operate the specific medical device 10.

For authentication using the second communication channel, the medical device 10, in one embodiment, is adapted to output an acoustic signal, for example a predetermined or random sequence of tones, which can comprise several different tones, by means of the loudspeaker 17, and the portable authentication device 20, in particular its control unit 21, is adapted to generate a signal, in particular a data signal, based on the received acoustic signal when the acoustic signal is received by means of the microphone 26, which contains a signal which corresponds to the received acoustic signal, and to transmit the generated signal wirelessly to the medical device 10 by means of the communication unit 22.

Since the acoustic signal emitted by the medical device 10 can be received by the portable authentication device 20 only when the latter is located at a position where acoustic communication between the medical device 10 and the portable authentication device 20 is possible, the medical device 10 determines on the basis of the reception of the signal comprising the signal corresponding to the acoustic signal received from the portable authentication device 20, that the portable authentication device 20 is located at a position where acoustic communication between the medical device 10 and the portable authentication device 20 is possible.

If, however, the medical device 10 does not receive a signal containing the signal corresponding to the received acoustic signal after a predetermined period of time has elapsed after the acoustic signal has been transmitted by the portable authentication device 20, the medical device 10 determines that the portable authentication device 20 is not located at a position where acoustic communication between the medical device 10 and the portable authentication device 20 is possible.

According to another embodiment, the medical device 10 is adapted to wirelessly transmit a signal, in particular a data signal, by means of the communication device 12, which contains a signal which corresponds to an acoustic signal, for example a predetermined or random sequence of tones, and the portable authentication device 20, in particular its control unit 21, is adapted, when receiving the signal containing the signal corresponding to the acoustic signal by means of the communication unit 22, to generate an acoustic signal based on the received signal, which corresponds to the signal corresponding to the acoustic signal, and to output the generated acoustic signal by means of the loudspeaker 25.

Since the acoustic signal transmitted by the portable authentication device 20 can only be received by the microphone 18 of the medical device 10 when the portable authentication device 20 is located at a position where acoustic communication between the medical device 10 and the portable authentication device 20 is possible, the medical device 10 determines based on the reception of the acoustic signal that the portable authentication device 20 is located at a position where acoustic communication between the medical device 10 and the portable authentication device 20 is possible.

On the other hand, if the medical device 10 does not receive an acoustic signal corresponding to the signal corresponding to the acoustic signal after a predetermined period of time has elapsed after the transmission of the signal containing the signal corresponding to the acoustic signal, the medical device 10 determines that the portable authentication device 20 is not located at a position where acoustic communication between the medical device 10 and the portable authentication device 20 is possible.

An advantage of this embodiment is that if the user of the portable authentication device 20 is not in the immediate vicinity of the medical device 10, for example in the event of a man-in-the-middle attack, the user is informed or warned that a man-in-the-middle attack is currently taking place by playing the sequence of tones by means of the loudspeaker 25 of the portable authentication device 20.

In a preferred embodiment, an individual identification number is stored in the memory device 13 of the medical device 10 which uniquely identifies the medical device 10 or is different from identification numbers stored in memory devices of others of the plurality of medical devices. In this case, the signal output by the communication device 12 and containing the signal corresponding to the acoustic signal may further contain a signal corresponding to the individual identification number stored in the memory device 13. The portable authentication device 20 can then, after receiving the signal transmitted by the medical device 10, output on the input/output unit 24, in particular on its display, the identification number of the medical device 10, enabling the user to identify the medical device 10 and, if appropriate, prevent an access to the medical device 10 by an unauthorized user.

In a preferred embodiment, the predetermined sequence of tones is determined by the identification number of the medical device 10 in such a way that different medical devices 10 output different sequences of tones. In this way, the user can advantageously quickly recognize on which medical device 10 he is authenticating himself to.

According to a further embodiment, the portable authentication device 20 is adapted to wirelessly transmit a signal, in particular a data signal, by means of the communication unit 22 when a wireless communication connection has been successfully established between the medical device 10 and the portable authentication device 20, which signal contains a signal which corresponds to an acoustic signal, for example a predetermined or random sequence of tones. In this case, the medical device 10, in particular its communication device 12, is adapted to receive the signal containing the signal corresponding to the acoustic signal, to generate, by means of the control device 11, an acoustic signal corresponding to the signal corresponding to the acoustic signal based on the received signal, and to output the generated acoustic signal to the portable authentication device 20 by means of the loudspeaker 17. The portable authentication device 20 is adapted to receive the acoustic signal by means of the microphone 26 and, upon receipt of the acoustic signal, to transmit wirelessly a signal, in particular a data signal, by means of the communication unit 22 to the medical device 10, which indicates that the portable authentication device 20 has received the acoustic signal. The medical device 10, in particular its control device 11, is adapted to determine whether or not the portable authentication device 20 is located at a position where acoustic communication between the medical device 10 and the portable authentication device 20 is possible, depending on whether or not it receives the signal indicating that the portable authentication device 20 has received the acoustic signal by means of the communication device 12.

Since the acoustic signal transmitted by the medical device 10 is receivable only by the portable authentication device 20 when the latter is located at a position where acoustic communication between the medical device 10 and the portable authentication device 20 is possible, the medical device 10 determines, based on the reception of the signal indicating that the portable authentication device 20 has received the acoustic signal, that the portable authentication device 20 is located at a position where acoustic communication between the medical device 10 and the portable authentication device 20 is possible.

However, if the medical device 10 does not receive a signal indicating that the portable authentication device 20 has received the acoustic signal after a predetermined period of time has elapsed after the transmission or output of the acoustic signal from the portable authentication device 20, the medical device 10 determines that the portable authentication device 20 is not located at a position where acoustic communication between the medical device 10 and the portable authentication device 20 is possible.

According to another different embodiment, the portable authentication device 20 is adapted to output a predetermined acoustic signal, preferably a predetermined sequence of tones, by means of the loudspeaker 25, when a wireless communication connection between the medical device 10 and the portable authentication device 20 has been successfully established. In doing so, the medical device 10 is adapted to determine, depending on whether or not it receives the predetermined acoustic signal, whether or not the portable authentication device 20 is located at a position where acoustic communication between the medical device 10 and the portable authentication device 20 is possible.

Since the predetermined acoustic signal output by the portable authentication device 20 can only be received by the medical device 10 when the portable authentication device 20 is located at a position where acoustic communication between the medical device 10 and the portable authentication device 20 is possible, the medical device 10 determines based on the reception of the predetermined acoustic signal that the portable authentication device 20 is located at a position where acoustic communication between the medical device 10 and the portable authentication device 20 is possible.

However, if the medical device 10 does not receive the predetermined acoustic signal after a predetermined period of time has elapsed after the wireless communication between the medical device 10 and the portable authentication device 20 has been successfully established, the medical device 10 determines that the portable authentication device 20 is not located at a position where acoustic communication between the medical device 10 and the portable authentication device 20 is possible.

If the medical device 10 determines that the user to whom the corresponding authentication signal is assigned is authorized to operate the specific medical device 10 and further determines that the portable authentication device 20 is located at a position where acoustic communication between the medical device 10 and the portable authentication device 20 is possible, the medical device 10 determines that authentication was successful and enables access to the medical device 10 within the scope of the authorizations assigned to the authentication signal in the authorization database.

On the other hand, if the medical device 10 determines that the user to whom the corresponding authentication signal is assigned is not authorized to operate the specific medical device 10, or determines that the portable authentication device 20 is not located at a position where acoustic communication between the medical device 10 and the portable authentication device 20 is possible, the medical device 10 determines that the authentication was not successful and blocks an access to the medical device 10.

According to a preferred embodiment, patient data and/or operating parameters of the medical device 10 assigned to the patient data, which were recorded during a treatment of the patient by means of the medical device 10, can be stored or are stored in the memory device 13 of the medical device 10, wherein the display of the input/output device 14 is adapted to display the patient data and/or the operating parameters of the medical device 10 assigned to the patient data. In this case, the medical device 10 is further arranged such that a user can only cause the patient data stored in the memory device 13 of the medical device 10 and/or the operating parameters of the medical device 10 assigned to the patient data stored in the memory device 13 to be displayed on the display of the input/output device 14 by means of an input using the input/output device 14 if the medical device 10 determines that authentication is successful.

Thus, according to this preferred embodiment, unauthorized access to the patient data stored in the memory device 13 of the medical device 10, such as name, age, patient identification number, patient history, and the like, as well as unauthorized access to operating parameters of the medical device 10 recorded during treatment of the patient and stored in the memory device 13 of the medical device 10 and assigned to the patient can be prevented or at least made more difficult.

In a particularly preferred embodiment, the patient data and/or the operating parameters assigned to the patient data and stored in the memory device 13 of the medical device 10 can be transferred by a user into the memory unit 23 of the portable authentication device 20 only if the medical device 10 determines that the authentication is successful, by means of the wireless communication connection between the medical device 10 and the portable authentication device 20.

In summary, the preferred two-channel authentication process can ensure the functional security of the treatment system and in particular of the medical device 10 and make man-in-the-middle attacks more difficult. In addition, the user is additionally informed about an authentication process taking place by outputting the acoustic signal by means of the loudspeaker 17 of the medical device 10 or the loudspeaker 25 of the portable authentication device 20.

The invention claimed is:

1. A treatment system for treating a patient, comprising: a medical device, and a portable authentication device, wherein the medical device and the portable authentication device are adapted to communicate wirelessly with each other, the medical device is adapted to output an acoustic signal when a wireless communication connection between the medical device and the portable authentication device is successfully established, the portable authentication device is adapted to receive the acoustic signal, to generate, based on the received acoustic signal, a signal containing a signal corresponding to the received acoustic signal, and to wirelessly transmit the generated signal to the medical device, and the medical device is adapted to determine whether or not the portable authentication device is located at a position where acoustic communication between the medical device and the portable authentication device is possible, depending on whether or not it receives the signal containing the signal corresponding to the acoustic signal received by the portable authentication device.

2. The treatment system according to claim 1, wherein the acoustic signal is a random or predetermined sequence of tones, and the signal containing the signal corresponding to the acoustic signal contains a signal corresponding to the random or the predetermined sequence of tones.

3. The treatment system according to claim 1, wherein the acoustic signal is a predetermined sequence of tones, the signal containing the signal corresponding to the acoustic signal contains a signal corresponding to the predetermined sequence of tones, and the tone sequence is determined by an individual identification number uniquely identifying the medical device.

4. The treatment system according to claim 1, wherein the medical device and the portable authentication device are adapted to communicate wirelessly with each other via a common radio standard and/or the medical device and the portable authentication device are adapted to communicate wirelessly with each other via an infrared signal.

5. The treatment system according to claim 1, wherein the medical device is adapted to wirelessly transmit an information-retrieval signal, for retrieving authentication information, to the portable authentication device and to wirelessly receive an authentication signal, the portable authentication device is adapted to transmit, cyclically and/or after receiving the information-retrieval signal, the authentication signal containing information identifying the portable authentication device, the medical device is adapted to perform, upon receipt of the authentication signal from the portable authentication device, an authentication in which it is verified whether or not the authentication signal is assigned to a user registered in an authorization database or to a portable authentication device registered in the authorization database, and whether or not the portable authentication device is located at a position where an acoustic communication between the medical device and the portable authentication device is possible, and to determine that the authentication is successful if the authentication signal is assigned to a user registered in an authorization database or to a portable authentication device registered in the authorization database and the portable authentication device is located at a position where acoustic communication between the medical device and the portable authentication device is possible.

6. The treatment system according to claim 5, wherein the medical device further comprises:

a memory device in which patient data and/or operating parameters of the medical device assigned to the patient data, which parameters were recorded during a treatment of the patient, can be stored, and an input/output device comprising a display for displaying the patient data and/or the operating parameters of the medical device assigned to the patient data, wherein a user can only cause the patient data stored in the memory device and/or the operating parameters of the medical device assigned to the patient data and stored in the memory device to be displayed on the display of the input/output device by means of an input using the input/output device if the medical device determines that the authentication is successful.

7. The treatment system according to claim 1, wherein the portable authentication device is designed as a mobile telephone or as a portable computer.

8. The treatment system according to claim 1, wherein the medical device is a dialysis device adapted to perform a dialysis treatment.

9. A method for verifying authentication of the portable authentication device for the treatment system of claim 1, the method comprising:

outputting an acoustic signal by the medical device, receiving the acoustic signal by the portable authentication device, generating, based on the received acoustic signal, by the portable authentication device, a signal containing a signal corresponding to the received acoustic signal, and wirelessly transmitting the generated signal to the medical device by the portable authentication device, and determining, by the medical device, depending on whether or not it receives the signal containing the signal corresponding to the acoustic signal received by the portable authentication device, whether or not the portable authentication device is located at a position where acoustic communication between the medical device and the portable authentication device is possible.

10. A treatment system for treating a patient, comprising:
a medical device, and
a portable authentication device, wherein
the medical device and the portable authentication device
are adapted to communicate wirelessly with each other,
the medical device is adapted to wirelessly transmit a
signal containing a signal corresponding to an acoustic
signal when a wireless communication connection is
successfully established between the medical device
and the portable authentication device,
the portable authentication device is adapted to receive
the signal containing the signal corresponding to the
acoustic signal, to generate, based on the received
signal, an acoustic signal corresponding to the signal
corresponding to the acoustic signal, and to output the
generated acoustic signal to the medical device, and
the medical device is adapted to determine whether or not
the portable authentication device is located at a posi-
tion where acoustic communication between the medi-
cal device and the portable authentication device is
possible, depending on whether or not it receives the
acoustic signal.

11. The treatment system according to claim 10, wherein
the medical device comprises a memory device in which an
individual identification number is stored which uniquely
identifies the medical device,
the medical device is adapted to also transmit, in the
signal containing a signal corresponding to the acoustic
signal, a signal corresponding to the individual identi-
fication number stored in the memory device, and
the portable authentication device comprises an input/
output device having a display and is adapted to output
the individual identification number on the display after
receipt of the signal transmitted by the medical device.

12. The treatment system according to claim 11, wherein
the medical device is adapted to wirelessly transmit an
information-retrieval signal, for retrieving authentication
information, to the portable authentication device and to
wirelessly receive an authentication signal,
the portable authentication device is adapted to transmit
cyclically and/or after receiving the information-re-
trieval signal an authentication signal containing infor-
mation identifying the portable authentication device,
the medical device is adapted to perform an authentication
upon receipt of the authentication signal from the
portable authentication device, in which it is verified
whether or not the authentication signal is assigned to
a user registered in an authorization database or to a
portable authentication device registered in the autho-
rization database, and whether or not the portable
authentication device is located at a position where an
acoustic communication between the medical device
and the portable authentication device is possible, and
to determine that the authentication is successful if the
authentication signal is assigned to a user registered in
an authorization database or to a portable authentica-
tion device registered in the authorization database and
the portable authentication device is located at a posi-
tion where acoustic communication between the medi-
cal device and the portable authentication device is
possible, wherein
in the memory device patient data and/or operating
parameters of the medical device assigned to the patient
data, which have been recorded during a treatment of
the patient, can be stored, and
the medical device further comprises an input/output
device having a display for displaying the patient data and/or the operating parameters of the medical device
assigned to the patient data, wherein
a user can only cause the patient data stored in the
memory device and/or the operating parameters of the
medical device assigned to the patient data stored and
in the memory device to be displayed on the display of
the input/output device by means of an input using the
input/output device if the medical device determines
that the authentication is successful.

13. A method for verifying authentication of the portable
authentication device for the treatment system of claim 10,
the method comprising:
wirelessly transmitting, by the medical device, a signal
containing a signal corresponding to an acoustic signal,
receiving the signal corresponding to the acoustic signal,
by the portable authentication device, generating, based
on the received signal, an acoustic signal corresponding
to the signal corresponding to the acoustic signal, by
the portable authentication device, and outputting the
generated acoustic signal to the medical device, and
determining, by the medical device, whether or not the
portable authentication device is located at a position
where acoustic communication between the medical
device and the portable authentication device is pos-
sible, depending on whether or not it receives the
acoustic signal.

14. A treatment system for treating a patient, comprising:
a medical device, and
a portable authentication device, wherein
the medical device and the portable authentication device
are adapted to communicate wirelessly with each other,
the portable authentication device is adapted to wirelessly
transmit a signal containing a signal corresponding to
an acoustic signal when a wireless communication
connection between the medical device and the por-
table authentication device is successfully established,
the medical device is adapted to receive the signal con-
taining the signal corresponding to the acoustic signal,
to generate, based on the received signal, an acoustic
signal corresponding to the signal corresponding to the
acoustic signal, and to output the generated acoustic
signal to the portable authentication device,
the portable authentication device is adapted to receive
the acoustic signal and to wirelessly transmit a signal to
the medical device indicating that the portable authen-
tication device has received the acoustic signal upon
receipt of the acoustic signal, and
the medical device is adapted to determine whether or not
the portable authentication device is located at a posi-
tion where acoustic communication between the medi-
cal device and the portable authentication device is
possible, depending on whether or not it receives the
signal indicating that the portable authentication device
has received the acoustic signal.

15. A method for verifying authentication of the portable
authentication device for the treatment system of claim 14,
the method comprising:
wirelessly transmitting a signal containing a signal cor-
responding to an acoustic signal by the portable authen-
tication device,
receiving, by the medical device, the signal containing the
signal corresponding to the acoustic signal, generating,
based on the received signal, by the medical device, an
acoustic signal corresponding to the signal correspond-
ing to the acoustic signal, and outputting, by the
medical device, the generated acoustic signal to the
portable authentication device, wirelessly transmitting, by the portable authentication device, a signal indicating that the portable authentication device has received the acoustic signal, to the medical device if the portable authentication device has received the acoustic signal from the medical device; and determining, by the medical device, depending on whether or not it receives the signal indicating that the portable authentication device has received the acoustic signal, whether or not the portable authentication device is located at a position where acoustic communication between the medical device and the portable authentication device is possible.

16. A treatment system for treating a patient, comprising:

a medical device, and a portable authentication device, wherein the medical device and the portable authentication device are adapted to communicate wirelessly with each other, the portable authentication device is adapted to output a predetermined acoustic signal, when a wireless communication connection between the medical device and the portable authentication device is successfully established, and the medical device is adapted to determine whether or not the portable authentication device is located at a position where acoustic communication between the medical device and the portable authentication device is possible, depending on whether or not it receives the predetermined acoustic signal.

17. A method for verifying authentication of the portable authentication device for the treatment system of claim 16, the method comprising:

outputting a predetermined acoustic signal, by the portable authentication device, and determining, by the medical device, depending on whether or not it receives the predetermined acoustic signal, whether or not the portable authentication device is located at a position where acoustic communication between the medical device and the portable authentication device is possible.

* * * * *